(12) United States Patent
Sacher

(10) Patent No.: US 8,331,009 B2
(45) Date of Patent: Dec. 11, 2012

(54) METHOD FOR MIXING COLORS IN A DISPLAY UNIT

(75) Inventor: Friedrich-Josef Sacher, Troisdorf (DE)

(73) Assignee: ASPRE AG, Appenzell (CH)

( * ) Notice: Subject to any disclaimer, the term of this patent is extended or adjusted under 35 U.S.C. 154(b) by 740 days.

(21) Appl. No.: 11/920,657

(22) PCT Filed: May 18, 2006

(86) PCT No.: PCT/EP2006/004742
§ 371 (c)(1),
(2), (4) Date: May 10, 2010

(87) PCT Pub. No.: WO2006/125563
PCT Pub. Date: Nov. 30, 2006

(65) Prior Publication Data
US 2010/0232006 A1    Sep. 16, 2010

(30) Foreign Application Priority Data

May 21, 2005  (DE) .......................... 10 2005 023 617

(51) Int. Cl.
*G02B 26/00* (2006.01)
(52) U.S. Cl. .......... 359/290; 359/291; 359/245; 359/237
(58) Field of Classification Search .............. 359/290, 359/291, 237
See application file for complete search history.

(56) References Cited

U.S. PATENT DOCUMENTS

| 6,037,955 A | 3/2000 | DeBoer et al. |
| 6,747,777 B1 | 6/2004 | Sikora et al. |
| 7,834,845 B2 * | 11/2010 | Sacher .......................... 345/107 |
| 2005/0099666 A1 | 5/2005 | Kodama et al. |

FOREIGN PATENT DOCUMENTS

| DE | 102 37 069 A1 | 2/2004 |
| EP | 1090384 | 1/2000 |
| EP | 1 529 274 B1 | 10/2006 |
| JP | 2005-84331 | 3/2005 |
| WO | WO2004/068208 A1 | 8/2004 |
| WO | WO2004/079439 | 9/2004 |

* cited by examiner

*Primary Examiner* — James Jones
(74) *Attorney, Agent, or Firm* — Muirhead and Saturnelli, LLC

(57) ABSTRACT

Disclosed is a method for mixing colors in a display unit with pixels that are arranged like a raster. According to said method, each pixel is provided with at least three color mirrors which are disposed behind or next to each other and are formed by transparent receptacles whose interiors are connected to reservoirs via ducts, while a colored liquid, e.g. a red liquid, as well as a fully transparent medium that is immiscible with colored liquid can be moved into the color mirrors and the reservoirs thereof, the fully transparent medium having the effect of making the color of the background in the color mirror appear white, for example. According to the invention, color is mixed by alternately moving the colored liquid and the fully transparent medium into the color mirrors in a rapid sequence, the time fraction during which the colored liquid or the fully transparent medium is located in the color mirror being controllable. In addition, the three colored liquids of the color mirrors of a pixel can be mixed so as to be successively and alternately moved into the color mirrors thereof in a rapid sequence, the time fraction during which the respective color is located in the color mirror being controllable.

17 Claims, No Drawings

METHOD FOR MIXING COLORS IN A DISPLAY UNIT

TECHNICAL FIELD

This application relates to a method for mixing colors in a display unit having a raster-like arrangement of pixels, each pixel being provided with at least three color levels arranged one behind the other or side by side, each color level being formed by shallow transparent chambers whose interiors are connected to reservoirs via channels, a colored liquid plus a clear colorless transparent medium that is not miscible with the colored liquid being movable into the color levels and their reservoirs. These display units work with direct light as well as backlighting.

BACKGROUND OF THE INVENTION

If the color levels of a pixel are arranged one behind the other, then the chambers must be made of a clear transparent material and the colored liquid must be transparent. Furthermore, a white or silvery white reflective layer must be arranged behind the color levels if it is a direct-light display.

If the color levels of a pixel are arranged side by side in a direct-light display, the bottom of the color level may be white or black and—if the color level is made of a clear transparent material—a white or black surface may be arranged behind the color levels, so the color level appears white or black when filled with the clear colorless transparent medium.

In the square design, the pixels and their color levels have an edge length of less than 3 mm and a volume of less than 0.5 mm$^3$. The colored liquid may be conveyed into the color levels by micropumps, piezoactuators, electrowetting, or compressed gas. If the color levels of a pixel are arranged one behind the other, then the colors are mixed subtractively by using the three secondary colors cyan, magenta, and yellow. These colors act as filters, with cyan filtering the primary color red out of white light and magenta filtering the primary color green out of white light, while yellow filters the primary color blue out of white light. If the three filters cyan, magenta, and yellow are stacked one above the other, then the three primary colors red, green, and blue and thus the light are filtered out, so the pixel appears black.

Mixing of color by subtractive and additive methods as well as display units of the type defined above are known from the patents EP 1 090 384, U.S. Pat. No. 6,037,955, and U.S. Pat. No. 6,747,777.

Although it is theoretically possible to produce all colors by mixing primary colors or secondary colors, in practice it is extremely difficult visually and in terms of control technology to produce the optimal hue and the correct color intensity in relatively small color levels and pixels and to do so in direct light, which is often variable.

Accordingly, it would be desirable to provide a method with which mixing of colors is facilitated.

SUMMARY OF THE INVENTION

In a display unit according to an embodiment of the system described herein, mixing of colors may be performed in such a way that the colored liquid and the clear transparent medium are moved into the color levels in alternation and in rapid succession, the time portion during which the colored liquid or the clear transparent medium is located in the color level being controllable.

DETAILED DESCRIPTION OF VARIOUS EMBODIMENTS

The rate at which the colored liquid and the clear colorless transparent medium must be changed in the color level depends on the inertia of the human eye in perceiving individual color changes. A frequency of ten color changes per second may be sufficient. However, color changing at a higher frequency is readily possible. For example, if two color levels are filled with clear colorless transparent medium in a direct-light display in which the pixels are composed of three color levels arranged one behind the other, with a white reflective layer arranged behind them, then only the colored liquid filled into the third color level determines the color of the pixel. This color may be lightened by conveying the colored liquid and the clear colorless transparent medium into the color levels in rapid succession. The color of a pixel is lighter when the time portion spent by the clear transparent medium in the color level is larger.

A rapid change of colored liquid and clear colorless transparent liquid is possible only within a color level. Within the three color levels of one pixel, however, the colors red, green, blue or cyan, magenta and yellow are miscible by rapid changing of colored liquids. The time portion during which the cyan or magenta or yellow colored liquids are in their color levels is controlled.

The greater the time portion of one colored liquid, the more decisive is the contribution of this colored liquid to the perceptible mixed color of the pixel.

The color change may occur with a frequency of 24 Hz to 30 Hz—like display refreshing in movie film. The frequency may also be increased, if necessary. If blue colored liquid is being moved into the color levels for 33.3% of the time in a second, yellow colored liquid is being moved into the color levels for 33.3% of that time, and clear colorless transparent liquid is being moved into the color levels for 33.3% of that time, then the pixel will appear light green. If the time portion for blue is increased at the expense of the time portion for yellow and colorless, then the color of the pixel will tend toward dark green. In addition to mixing two colored liquids and a clear transparent liquid, time-dependent mixing of three colors, i.e., three colored liquids red, green, blue or cyan, magenta, yellow is possible.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for mixing colors in a display unit having a raster arrangement of pixels in which each pixel has at least three color levels arranged one behind the other or side by side, formed by transparent chambers having interiors that are connected to reservoirs via channels, a colored liquid plus a clear transparent medium not miscible with the colored liquid being movable into the color levels and the reservoirs, the method comprising:

moving the colored liquid and the clear transparent medium in alternation and in rapid succession into the color levels, a time portion during which the colored liquid or the clear transparent medium is located in the color levels being controllable, wherein a change between the colored liquid and the clear transparent medium moving into the color levels is controlled according to the time portion, and wherein the time portion dictates a perceived color of each pixel, wherein the change between the colored liquid and the clear transparent medium takes place at a frequency greater than 10 Hz.

2. The method as recited in claim 1, wherein the colored liquid is a transparent colored liquid and the clear transparent medium is a clear transparent liquid, wherein the liquids are in the color level and the reservoir connected thereto, and wherein the liquids are moved by an electrowetting technique, so that the colored liquid or the clear transparent liquid is located in the color level in alternation.

3. The method for mixing colors as recited in claim 1, wherein the display unit is a direct-light display in which a white or silvery white reflective layer is arranged behind the color levels, and wherein the time portion during which the clear transparent medium is located in the color levels of a pixel is increased to lighten a color.

4. A method for mixing colors in a display having a raster arrangement of pixels in which each pixel has at least three color levels arranged side by side or one behind the other, the color levels being formed by transparent chambers having interiors that are connected to reservoirs via channels and a colored liquid plus a clear transparent medium not miscible with the colored liquid are movable into the color levels and the reservoirs, the method comprising:

moving liquids of the three color levels of a pixel in alternation and in rapid succession into the color levels, a time portion during which the liquid of a color level or the liquid of another color level is located in the respective color level being controllable, wherein a change between the liquids moving into the color levels is controlled according to the time portion, and wherein the time portion dictates a perceived color of each pixel, wherein the liquids are moved among the color levels at a frequency greater than 10 Hz.

5. The method as recited in claim 1, wherein the liquids include a transparent colored liquid and a clear transparent liquid, wherein the liquids are in the color level and the reservoir connected thereto, wherein the liquids are moved by an electrowetting technique, so that the colored liquid or the clear transparent liquid is located in the color level in alternation, wherein the display unit is a direct-light display in which a white or silvery white reflective layer is arranged behind the color levels, and wherein the time portion during which the clear transparent medium is located in the color levels of a pixel is increased to lighten a color.

6. The method as recited in claim 2, wherein the transparent colored liquid is transparent ink.

7. The method as recited in claim 2, wherein the colored liquid is colored at least one of: cyan, yellow and magenta.

8. A method for mixing colors in a display unit, comprising:

moving a plurality of liquids in alternation into a plurality of chambers of at least one pixel of the display unit, wherein a time portion during which a particular one of the plurality of liquids is located in at least one of the chambers is controlled to determine a perceived color of the at least one pixel, wherein a change between particular ones of the plurality of liquids moving into the plurality of chambers is controlled according to the time portion, and wherein the time portion dictates the perceived color of the at least one pixel, wherein the plurality of liquids are moved into the chambers at a frequency greater than or equal to 10 Hz.

9. The method as recited in claim 8, wherein the plurality of liquids includes a colored liquid and a clear transparent liquid not miscible with the colored liquid.

10. The method as recited in claim 8, wherein the plurality of liquids includes two colored liquids.

11. The method as recited in claim 8, wherein the plurality of liquids includes two colored liquids and a clear transparent liquid not miscible with the colored liquids.

12. The method as recited in claim 8, wherein the plurality of liquids includes three colored liquids.

13. The method as recited in claim 12, wherein the three colored liquids are colored red, green and blue.

14. The method as recited in claim 12, wherein the three colored liquids are colored cyan, magenta and yellow.

15. The method as recited in claim 8, wherein the frequency is greater than 24 Hz.

16. The method as recited in claim 15, wherein the frequency is between 24 Hz and 30 Hz.

17. A method for mixing colors in a display unit, comprising:

moving a plurality of liquids in alternation into a plurality of chambers of at least one pixel of the display unit, wherein a time portion during which a particular one of the plurality of liquids is located in at least one of the chambers is controlled to determine a perceived color of the at least one pixel, wherein a change between particular ones of the plurality of liquids moving into the plurality of chambers is controlled according to the time portion, and wherein the time portion dictates the perceived color of the at least one pixel, wherein one of the plurality of liquids is a clear transparent liquid, and wherein the time portion during which the clear transparent liquid is located in the chambers is increased to lighten a color.

\* \* \* \* \*